(12) United States Patent
Caserta et al.

(10) Patent No.: US 8,718,454 B2
(45) Date of Patent: May 6, 2014

(54) MODULE FOR MANUFACTURING ELECTRIC VOLATILE SUBSTANCE EVAPORATORS

(75) Inventors: Andrea Caserta, Barcelona (ES); Ruben García Fábrega, Barcelona (ES); Ricard Tomás Vilarasa, Barcelona (ES)

(73) Assignee: Zobele Espana S.A. (ES)

( * ) Notice: Subject to any disclaimer, the term of this patent is extended or adjusted under 35 U.S.C. 154(b) by 629 days.

(21) Appl. No.: 12/529,026

(22) PCT Filed: Feb. 28, 2008

(86) PCT No.: PCT/EP2008/052426
§ 371 (c)(1),
(2), (4) Date: Oct. 8, 2009

(87) PCT Pub. No.: WO2008/107366
PCT Pub. Date: Sep. 12, 2008

(65) Prior Publication Data
US 2010/0034527 A1   Feb. 11, 2010

(30) Foreign Application Priority Data

Mar. 2, 2007   (ES) .................................. 200700562

(51) Int. Cl.
*F24F 6/08*   (2006.01)

(52) U.S. Cl.
USPC ............ 392/395; 392/386; 392/390; 392/405

(58) Field of Classification Search
None
See application file for complete search history.

(56) References Cited

U.S. PATENT DOCUMENTS

| 4,130,748 | A  | * | 12/1978 | Schwer ........................ 200/38 D |
| 6,104,866 | A  |   | 8/2000  | DeWitt et al. |
| 6,768,865 | B2 | * | 7/2004  | Stathakis et al. .............. 392/395 |
| 6,996,335 | B2 | * | 2/2006  | Zobele .......................... 392/395 |
| 7,379,662 | B2 | * | 5/2008  | Caserta et al. ................ 392/395 |

(Continued)

FOREIGN PATENT DOCUMENTS

| EP | 0976410 A1 | 2/2000 |
| ES | 2259020    | 9/2006 |

(Continued)

OTHER PUBLICATIONS

International Search Report PCT EP2008/052426; Dated: Jul. 3, 2008.

*Primary Examiner* — Thor Campbell
(74) *Attorney, Agent, or Firm* — Cantor Colburn LLP (57) ABSTRACT

The present invention generally relates to manufacturing electric volatile substance evaporators for evaporating aromatic substances and/or insecticides for example and the invention more specifically allows the modular construction of these types of devices such that based on a basic evaporator, a manufacturer of electric evaporators can incorporate additional elements to the device in order to produce different types of evaporators without altering the basic evaporator design, where the module comprises a casing having a first surface configured to be assembled with a volatile substance evaporator and internally carries an electric device intended to cooperate in the operation of the evaporator.

17 Claims, 9 Drawing Sheets

(56) References Cited

U.S. PATENT DOCUMENTS

| | | |
|---|---|---|
| 7,499,632 B2 * | 3/2009 | Granger et al. ............... 392/386 |
| 7,962,017 B2 * | 6/2011 | Viera ............................ 392/392 |
| 8,005,350 B2 * | 8/2011 | Zlotnik et al. ................ 392/395 |
| 8,135,265 B2 * | 3/2012 | Tollens et al. ................ 392/395 |
| 2002/0172512 A1 * | 11/2002 | Stathakis et al. ............. 392/395 |
| 2004/0067172 A1 * | 4/2004 | Ehrlich et al. ................ 422/123 |
| 2005/0180736 A1 * | 8/2005 | Zobele .......................... 392/395 |
| 2008/0003132 A1 * | 1/2008 | McGee et al. ................... 422/4 |
| 2008/0226269 A1 * | 9/2008 | DeWitt et al. ................ 392/386 |
| 2008/0253755 A1 * | 10/2008 | Smith et al. ................... 392/386 |

FOREIGN PATENT DOCUMENTS

| | | |
|---|---|---|
| WO | 9738576 A1 | 10/1997 |
| WO | 9846281 A1 | 10/1998 |
| WO | 0226274 A2 | 4/2002 |
| WO | 2004/020002 | 3/2004 |
| WO | 2005079875 A1 | 9/2005 |
| WO | 2006/046209 | 5/2006 |

* cited by examiner

MODULE FOR MANUFACTURING ELECTRIC VOLATILE SUBSTANCE EVAPORATORS

TECHNICAL FIELD OF THE INVENTION

The present invention generally relates to manufacturing electric volatile substance evaporators for evaporating aromatic substances and/or insecticides for example.

More specifically the invention allows the modular construction of these types of devices such that based on a basic evaporator, a manufacturer of electric evaporators can incorporate additional elements to said device in order to produce different types of evaporators without altering the basic evaporator design.

The invention allows a considerable savings in the manufacturing costs of these types of products since a standard evaporator can be used in the manufacture in order to obtain different types of evaporators according to the needs.

BRIEF DISCUSSION OF RELATED ART

Electric volatile substance evaporators are widely known in the state of the art and are generally formed of a casing carrying a bottle containing the substance to be evaporated, as well as a wick of porous material partially immersed in said bottle. The wick is impregnated with the volatile substance and heating resistances arranged in said casing collaborate in evaporating the substance.

In the past few years the complexity of these evaporator devices has increased since different fittings involved in the operation and use of the evaporator have been incorporated. In this sense for example, several evaporators can have light or movement sensors, electronic timers, fans, etc. In the case of the light sensors, these can be used to control the operation of the evaporator, for example so that it only operates during the day or at night or that it begins operating only when turning on the light of the bathroom.

Electronic timers allow the evaporator to operate only during a preestablished time period which can be modified at will by the user so that it operates at certain time intervals for example.

However one of the more complex modifications of these types of devices is the incorporation of a fan, firstly due to the size thereof and secondly due to the fact that the air flow generated by the fan modifies the temperature of the heating elements and therefore also modifies the evaporation process. This makes the known evaporators incorporating a fan have a design that is very complex and completely different from standard designs of these types of devices, which logically makes their manufacturing cost increase.

Therefore in the current state of the art, manufacturers wishing to incorporate any complement to an electric evaporator are forced in most cases to design a completely new evaporator and logically order new molds and adapt the assembly process for manufacturing the new evaporator. This situation makes producing new evaporators more expensive and slows down the response of manufacturers to their clients' needs and to market demand.

This drawback is accentuated in the case of small manufacturers producing a small number of units each year, and for whom it is very expensive to offer their clients a new evaporator design mainly due to the costs of the molds for the plastic parts, making it difficult to be able to recover the cost of manufacturing a small number of units.

BRIEF SUMMARY OF THE INVENTION

The present invention satisfactorily solves the previously mentioned drawback by means of the subject matter defined in the attached claims. More specifically the invention relates to a universal module which can be easily mounted or assembled during the manufacture of an evaporator device or different types of standard evaporators. Thus with the module manufacturers can easily incorporate different complements to evaporators which are currently being manufactured without needing to make any substantial modification in the design and with minimum modifications in the assembly process thereof.

The invention preferably makes use of certain parts of the evaporator with a standard or standardized shape and size and which most of these types of devices have. This standardized part is used for coupling the module, therefore the latter can be coupled to most electric evaporators existing on the market. Specifically, to couple the module the inlet which the evaporator has can be used for receiving a plug base, therefore once the module is mounted it is located between the evaporator and a plug base.

Therefore one aspect of the invention relates to a module for manufacturing electric volatile substance evaporators comprising a casing in which a first surface configured to be assembled or mounted in a volatile substance evaporator is provided, said casing internally carrying an electric device intended to participate in the operation of the evaporator. The module further has a second surface in which electric terminals are integrated for their connection to a mains socket or said second surface can be configured to be assembled with a terminal base for its connection to the mains. In the second case, the second surface can have a plug base assembled or prepared for its assembly in the module.

The invention provides that the module is compact so that mounting it on an evaporator device does not result in too large a product. To that end the first and the second surfaces are arranged substantially parallel to one another, and the mentioned electric device, which for example can be a fan, is arranged between said first and second surfaces.

The invention also relates to a volatile substance evaporator device comprising a casing configured for carrying means for evaporating volatile substances and incorporating the previously described module. The electric device or the electronic means arranged in the module are intended to cooperate with the evaporation means of the evaporator, thus providing a complementary function of the evaporator, for example for increasing the reaching range of the evaporated substance by means of the action of a fan, or for example for controlling the operation time of the evaporator by means of a timer.

BRIEF DESCRIPTION OF THE DRAWINGS

To complement the description being made and for the purpose of aiding to better understand the features of the invention according to a preferred practical embodiment thereof, a set of drawings is attached as an integral part of said description, in which the following has been shown with an illustrative and non-limiting character:

FIG. 6(b) shows the left and right profile of the assembly and a front elevational view. FIG. 6(c) corresponds with a rear elevational view of the assembly and FIG. 6(d) corresponds with an upper plan view.

DETAILED DESCRIPTION OF THE INVENTION

Figure 1:
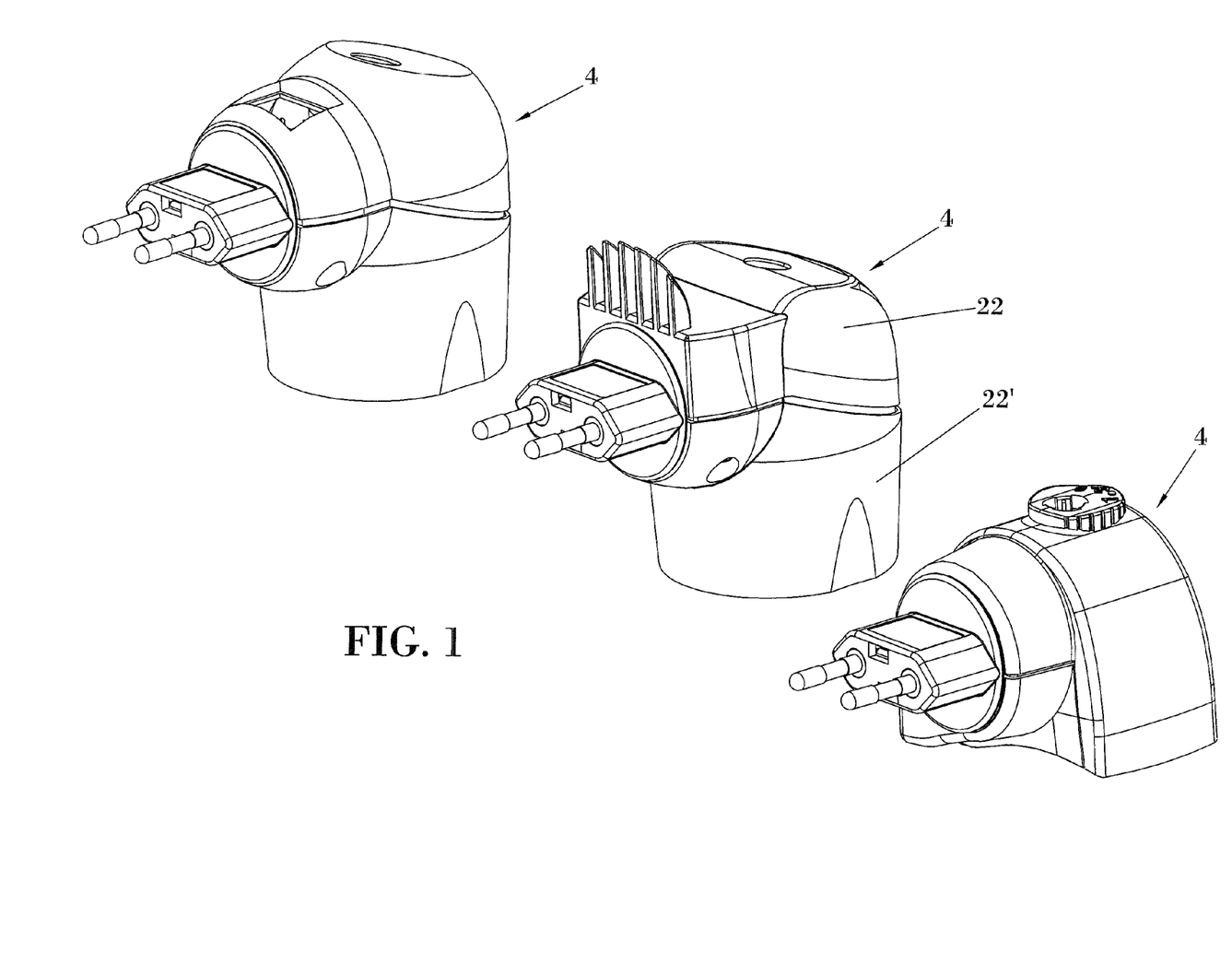
FIG. 1 shows three perspective views corresponding to three different designs of electric evaporators of the state of the art.

Three different types of electric volatile substance evaporators are depicted in FIG. 1, in which it can be observed that all of them have in common a standardized inlet for receiving a plug base.

Figure 2:
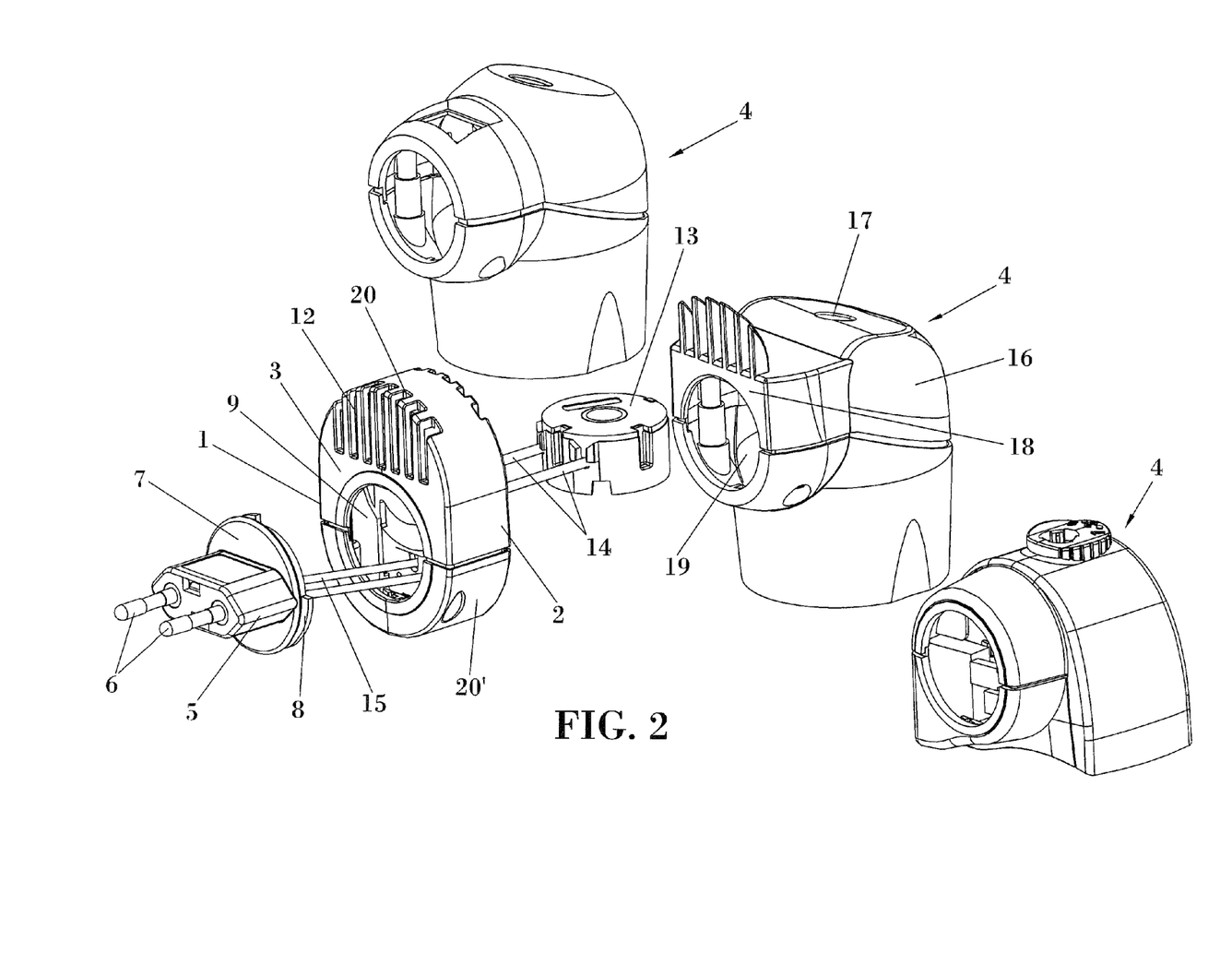
FIG. 2 shows a depiction similar to that of FIG. 1 in which the module has been added. This figure illustrates how the module can be assembled with different types of existing evaporators, in this case using the standardization of one of its parts such as the opening for assembling a universal socket for example.

FIG. 2 shows an embodiment of a module for manufacturing electric volatile substance evaporators formed from a casing (1) in which a first surface (2) which is configured to be assembled with a volatile substance evaporator device (4) is provided. The casing (1) internally carries an electric device, such as a fan or a timer for example, as a complement for the operation of the evaporator.

The casing (1) further has a second surface (3) intended to receive a plug base (5) having electric terminals (6) for its connection to a mains socket. In the preferred embodiment of FIG. 2, the plug base (5) has a circular platform (7) with a guide section (8) for coupling to the second surface (3) of the casing (1). In this embodiment, the configuration of the second surface (3) for its coupling to the plug base (5) consists of a circular window (9) sized so as to allow assembling the platform (7) of the base (5) such that the base can rotate at least 90° in order to be able to adopt both a vertical and horizontal position.

In another alternative embodiment, the plug base (5) can be integrated in the second surface (3) of the casing.

As can be observed in FIG. 2, the first and second surfaces (2,3) of the casing (1) are arranged substantially parallel to one another and the electric element, in this case a fan (23), is arranged between said first and second surfaces thus forming a smaller compact configuration. The respective circular windows of the first and second surfaces are arranged substantially opposite one another.

The configuration of the first surface (2) consists of anchoring means for its assembly with an evaporator device, and specifically said anchoring means comprise a circumferential wall (10) emerging from the first surface (2) and having a perimetric lip (11) on its free edge. The circumferential wall (10) internally demarcates a first circular window providing access to the inside of the casing (1).

The casing (1) is formed by two halves (20, 20') coupled to one another, and as observed in FIG. 2, the upper half (20) has ventilation openings (12) in correspondence with said first and second surfaces (2, 3) to allow the circulation of air through the casing.

The module can have a heating element (13) located outside the casing, and which is connected electrically with a printed circuit board (24) housed inside the casing by means of wires (14). Similarly, the plug base (5) is equally connected and joined to the casing (1) by means of wires (15) connected to the mentioned printed circuit board. The module with these components already connected can be supplied to evaporator manufacturers such that they only have to assemble this module when they wish to produce evaporators with an additional function instead of installing a heating element (13) directly connected to a plug base (5).

The module can additionally have electronic means for controlling the operation of said fan and/or the operation of the heating element, these means being able to consist of for example: an electronic timer, means for regulating the speed of the fan, light sensors, AC/DC converter or a push-button. The electronic components necessary for these functions are arranged in the printed circuit board (24).

In another alternative embodiment, the module has a lighting element (not depicted) intended to generate a lighting effect during the use of the device, such as providing a faint light during the night which can be projected through the bottle containing the volatile substance for example. For this functionality the casing (1) of the module is sized so that when it is coupled to the evaporator device, the mentioned lighting element is located near the mentioned bottle below the casing (4).

The shape of the casing of the module (1) is thus adapted so that the electric device housing either the fan (23), a lighting element or another type of device, can cooperate with the evaporator device, either through the outside of the casing (4) or through the inside, for example for driving air over the outlet hole (17) or illuminating the bottle of volatile substance.

The invention also relates to a volatile substance evaporator device (4) to which the previously described module has been incorporated. The evaporator device (4) is formed by a second casing (16) which is configured to carry means for evaporating volatile substances (not depicted) in a manner already known in the state of the art. These means consist of an active substance container, in which a lower portion of a wick is immersed for being impregnated with the substance to be evaporated, such that the upper portion of the wick is heated by a heating element (13). The casing (16) of the evaporator has an outlet hole (17) for the evaporated substance.

Figures 3A, 3B, 3C, 3D:
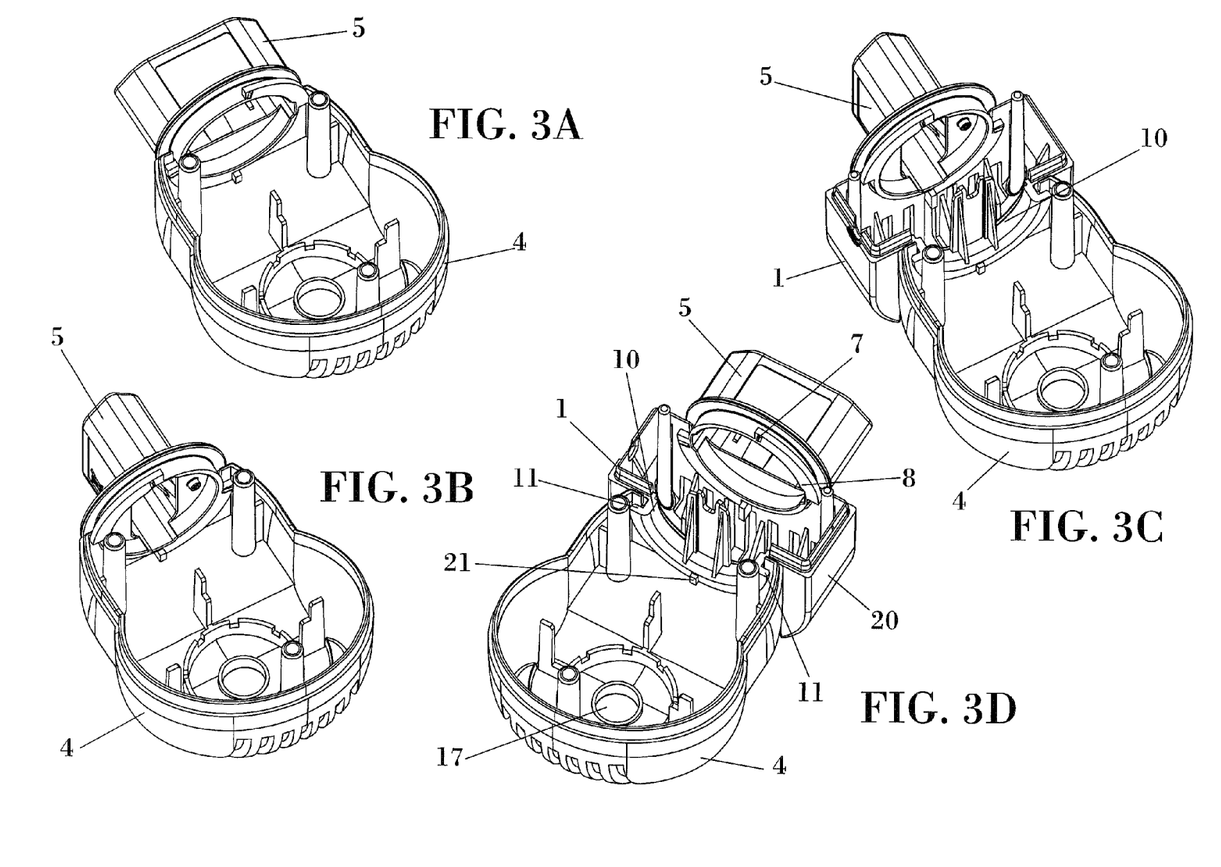
FIG. 3 shows several perspective views of two volatile substance evaporators in an inverted position and open for the purpose of showing the coupling between the evaporator and the module or the evaporator and a plug base. Figures (a) and (b) correspond with a conventional evaporator and Figures (c) and (d) depict an evaporator provided with the module of the invention with the plug base in different positions.
Figure 4A:
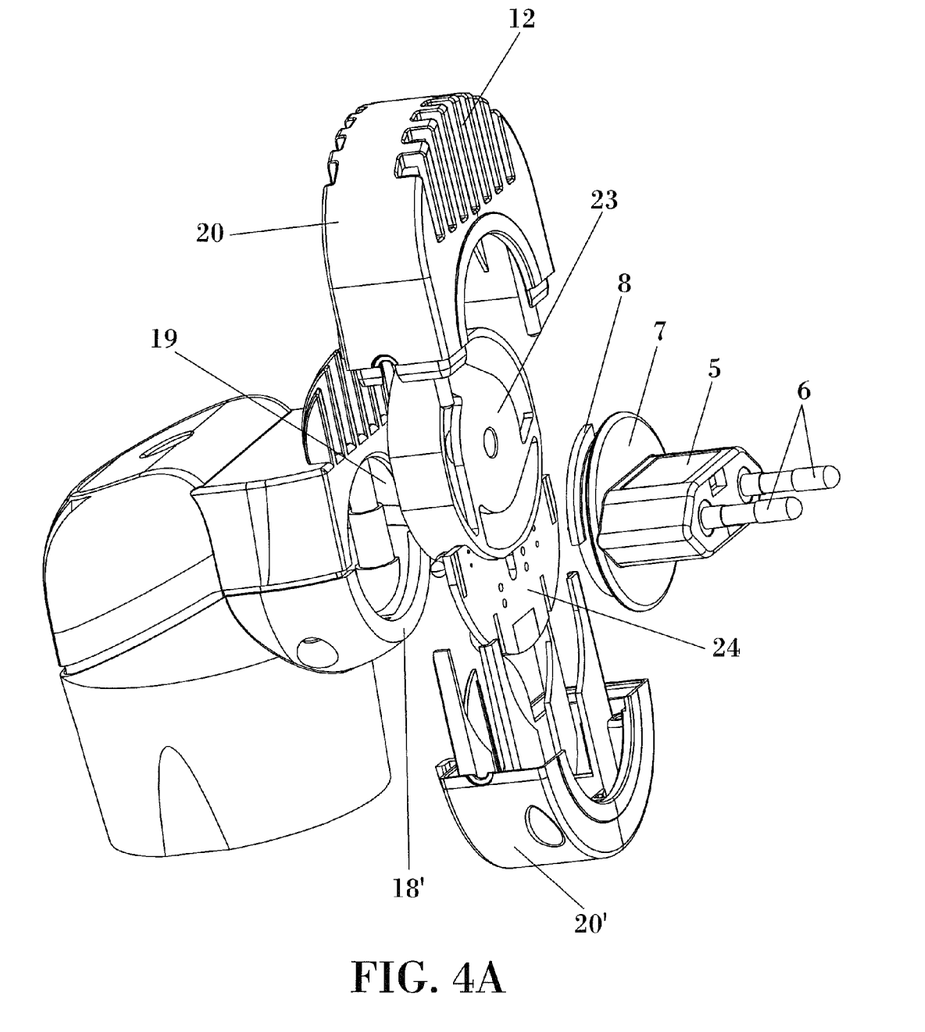
FIG. 4(a) shows a perspective view of the assembly with an exploded depiction of the module when it is not coupled to the evaporator.
Figure 4B:
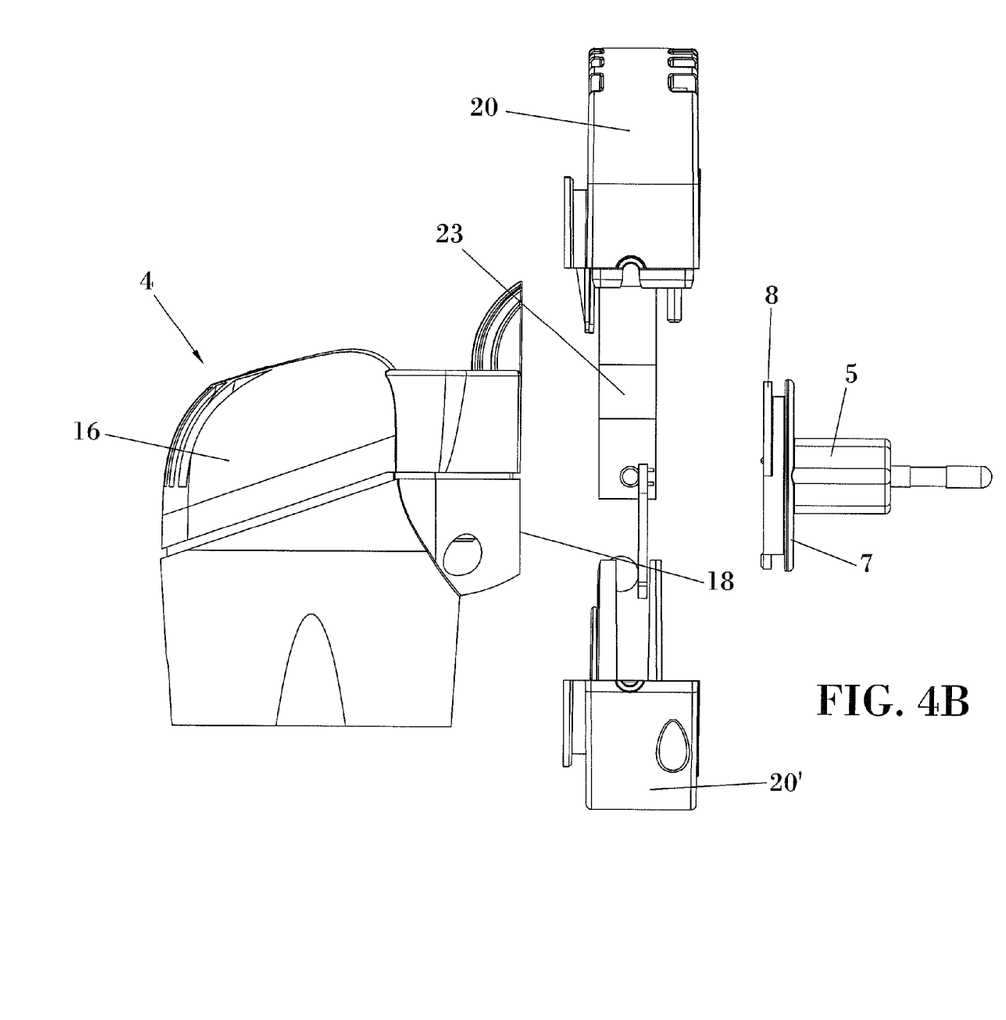
FIG. 4(b) is a side elevational view corresponding to FIG. 4(a).

The casing (16) of the evaporator has a third surface (18) configured to cooperate with the first surface (2) of the module for the assembly thereof. The configuration specifically consists of a circular window (19) sized in order to receive the circumferential wall (10) emerging from the first surface (2), as especially observed in FIGS. 3c and 3d.

In these same figures, it is observed how the base (7) by means of its guide (8) is set in the circular window (9) of the casing (1), and in turn the other side of the casing (1) by means of the perimetric lip (11) and the wall (10) is set in the window (19) of the evaporator device.

Both casings (20) and (16) are internally communicated for the passage of the wires (14) and (15) respectively connecting the heating element (13) and the plug base (5) with the printed circuit board existing in the module.

To prevent the rotation between casings (29) and (16), the casing (4) has a protuberance (21) housed in a notch existing for such purpose in the perimetric lip (11).

Figure 5A:
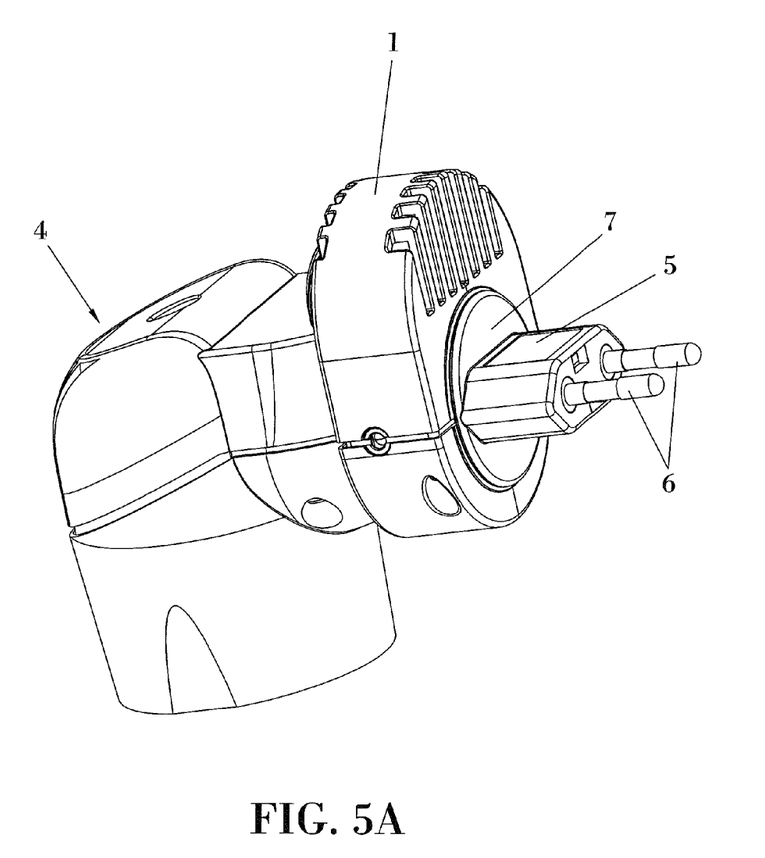
FIG. 5(a) shows a perspective view of the assembly when the module is coupled to the evaporator.
Figure 5B:
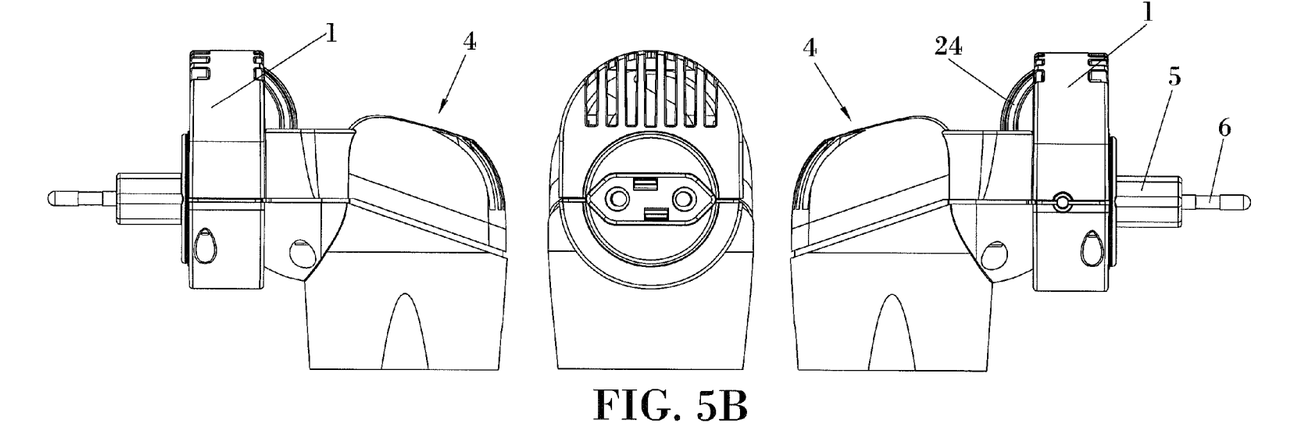
FIG. 5(b) shows the left and right profile of the assembly and a front elevational view.
Figure 5C:
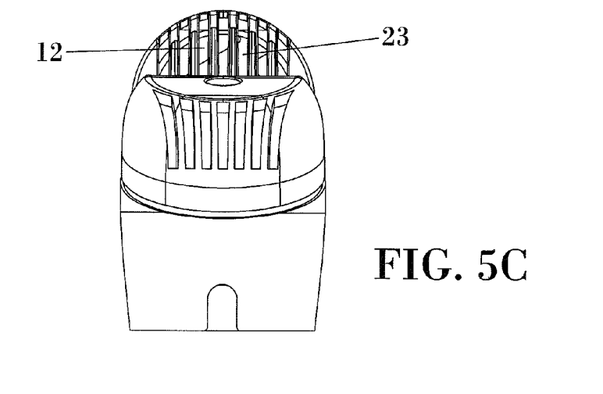
FIG. 5(c) corresponds with a rear elevational view of the assembly.
Figure 6A:
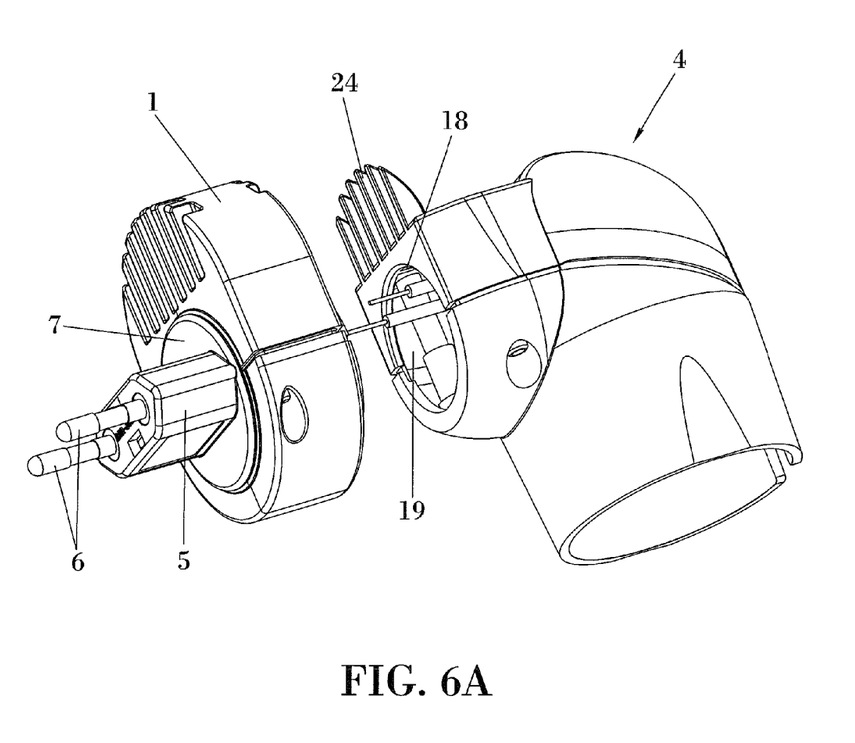
FIG. 6(a) shows a perspective view of the assembly when the module is decoupled from the evaporator.
Figures 6B, 6C, 6D:
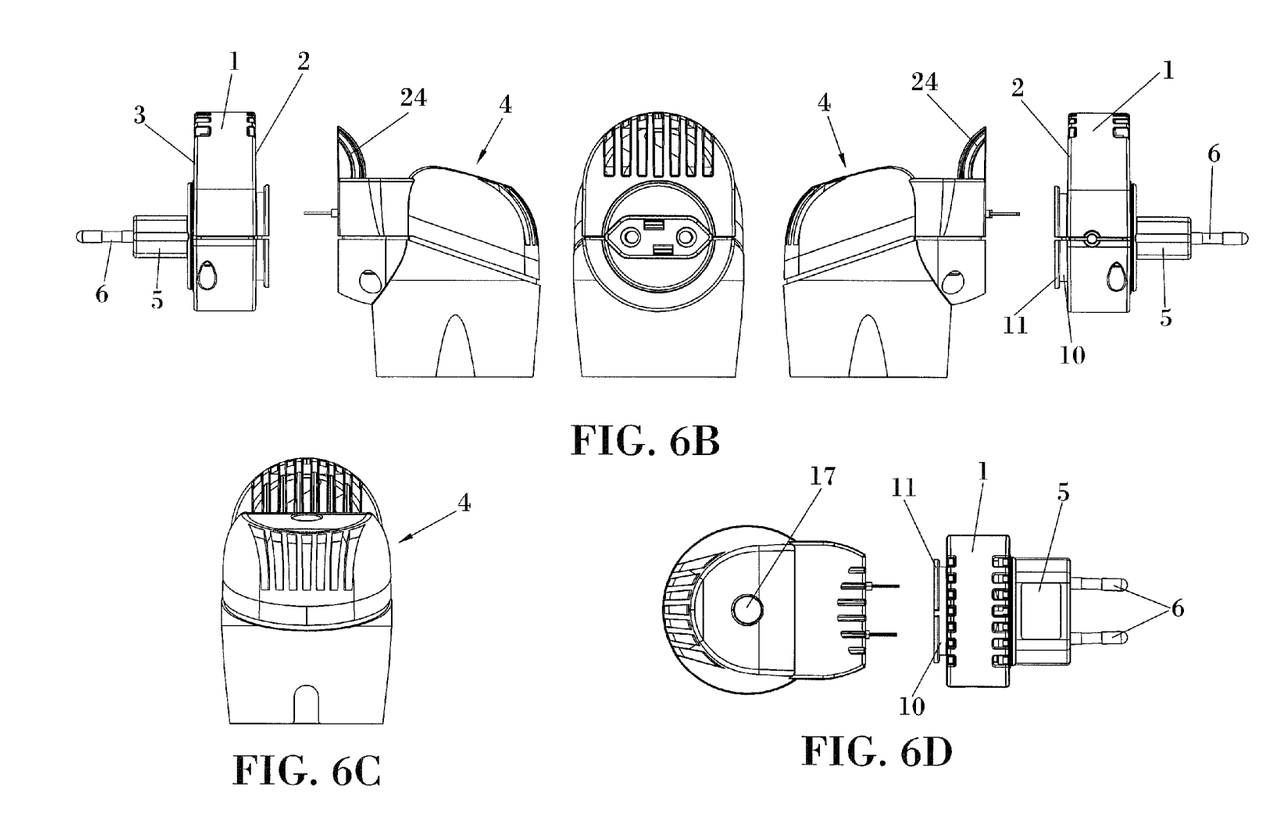

As especially observed in FIG. 5(b), once the casing (1) of the module is assembled to the evaporator device, the fan (23) is arranged to drive air out of the casing (16) of the evaporator, passing through the hole (17) for the purpose of driving the evaporated product and enhancing its diffusion. A grate (24) prevents any object from accidentally reaching the fan blades.

In order to assemble the module in the evaporator device, the previously assembled module is used, and upon joining the two parts (22,22') forming the casing (16) of the evaporator, the module is arranged so that the wall (10) of the module is trapped between both parts. The manufacturing process is thus not substantially altered since the previously described operation is also carried out in conventional evaporators for coupling the plug base to the evaporator.

Several possibilities of practical embodiments of the invention are described in the attached dependent claims.

In view of this description and set of drawings a person skilled in the art could understand that the claims of the invention which have been described can be combined in multiple ways. The invention has been described according to some preferred embodiments thereof, however for a person skilled in the art it will be evident that multiple variations can be introduced in said preferred embodiments.

The invention claimed is:

1. A module for manufacturing electric volatile substance evaporators, comprising:
   a casing and
   an electric device housed within said casing wherein said electric device is either a fan, a lighting element, or a timer,
   wherein said casing comprises a first surface provided with first anchoring means configured to be assembled with a circular opening of an electric volatile substance evaporator device, said circular opening of said evaporator device having a shape and dimension configured for receiving an electric plug base, the casing further comprising a second surface provided with second anchoring means configured to be assembled with the electric plug base,
   wherein the first and second surfaces are arranged substantially parallel to one another,
   wherein the electric device is arranged between said first and second surfaces,
   wherein said first anchoring means has a circumferential configuration, and a circumferential wall emerging from the first surface, said wall having a perimetric lip on its free edge,
   wherein the second anchoring means comprises a second circular window forming a circumferential edge, wherein the first surface has a first circular window within said circumferential wall, and
   wherein the first and second windows are arranged substantially opposite one another.

2. A module according to claim 1, wherein the first and second anchoring means are arranged substantially opposite each other.

3. A module according to claim 1, wherein the second surface has electric terminals for its connection to a mains socket.

4. A module according to claim 1, comprising a plug base assembled in said second surface wherein said base can rotate with respect to the casing.

5. A module according to claim 1, wherein the casing is formed by two parts coupled to one another.

6. A module according to claim 1, further comprising electronic means adapted for controlling the operation of said electric device.

7. A module according to claim 6, wherein said electronic means comprise at least one of means for regulating the speed of the fan, light sensors, and a push-button.

8. A module according to claim 1, further comprising a heating element located outside the casing and which is electrically connected with a printed circuit board housed inside the casing.

9. A module according to claim 8, further comprising electronic means for controlling an operation of said heating element, wherein said electronic means comprise at least one of an electronic timer, light sensors, movement sensor, and an AC/DC converter.

10. A module according to claim 1 wherein the casing has ventilation openings in said first and second surfaces to allow circulation of air therethrough.

11. An electric volatile substance evaporator device comprising a housing configured to carry means for evaporating volatile substances, wherein the evaporator device incorporates a module, the module comprising:
    a casing, and
    an electric device housed within said casing, wherein said electric device is either a fan, a lighting element, or a timer,
    wherein said casing includes a first surface provided with first anchoring means assembled with a circular opening of the electric volatile substance evaporator device, said circular opening of said electric evaporator device having a shape and dimension configured for an electric plug base,
    the casing further comprising a second surface provided with second anchoring means assembled with the electric plug base,
    wherein the first and second surfaces are arranged substantially parallel to one another,
    wherein the electric device is arranged between said first and second surfaces,
    wherein said first anchoring means have a circumferential configuration, and comprise a circumferential wall emerging from the first surface, said wall having a perimetric lip on its free edge,
    wherein the second anchoring means comprise a second circular window forming a circumferential edge, wherein the first surface has a first circular window within said circumferential wall, and
    wherein the first and second windows are arranged substantially opposite one another.

12. A device according to claim 11, wherein the casing of the device has a third surface configured to cooperate with the first surface of the module in the assembly of said module.

13. A device according to claim 12, wherein said third surface has a third circular window sized to receive the circumferential wall of the first surface.

14. A device according to claim 11, wherein the housing of the evaporator has an outlet hole for an evaporated substance, and the electric device is a fan arranged to drive air out of the housing of the evaporator and over said hole.

15. A device according to claim 11, wherein a lighting element housed in the housing of the module is arranged to illuminate an outer part of the evaporator device.

16. A device according to claim 11, wherein the means for evaporating active substances comprise an active substance container, a wick having a lower portion immersed said container and an upper portion emerging from said container, a heating element arranged to heat the upper portion of the wick.

17. A device according to claim 11, wherein the module cannot rotate with respect to the casing of the evaporator device.

* * * * *